(12) United States Patent
Featonby et al.

(10) Patent No.: US 10,073,048 B2
(45) Date of Patent: Sep. 11, 2018

(54) APPARATUS AND METHOD FOR SCANNING A STRUCTURE (71) Applicant: JOHNSON MATTHEY PUBLIC LIMITED COMPANY, London (GB)

(72) Inventors: Paul David Featonby, Northumberland (GB); Emanuele Ronchi, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 145 days.

(21) Appl. No.: 15/305,387

(22) PCT Filed: May 1, 2015

(86) PCT No.: PCT/GB2015/051280
§ 371 (c)(1),
(2) Date: Oct. 20, 2016

(87) PCT Pub. No.: WO2015/166266
PCT Pub. Date: Nov. 5, 2015

(65) Prior Publication Data
US 2017/0045465 A1  Feb. 16, 2017

(30) Foreign Application Priority Data
May 2, 2014  (GB) .................. 1407826.5

(51) Int. Cl.
G21K 1/02   (2006.01)
G01N 23/18  (2018.01)
G01N 9/00   (2006.01)

(52) U.S. Cl.
CPC .............. *G01N 23/18* (2013.01); *G01N 9/00* (2013.01); *G01N 2223/3301* (2013.01);
(Continued)

(58) Field of Classification Search
None
See application file for complete search history.

(56) References Cited

U.S. PATENT DOCUMENTS

| 4,143,273 A | 3/1979 | Richey et al. |
| 4,277,684 A | 7/1981 | Carson |

(Continued)

FOREIGN PATENT DOCUMENTS

| DE | 10017345 A1 | 10/2001 |
| DE | 10 2012205245 A1 | 10/2013 |

(Continued)

OTHER PUBLICATIONS

International Search Report, dated Aug. 28, 2015, from corresponding PCT application.

(Continued)

*Primary Examiner* — Hoon Song
(74) *Attorney, Agent, or Firm* — Baker & Hostetler LLP (57) ABSTRACT

An apparatus and method for scanning a structure for detecting variations in density of a structure, the apparatus (10) includes: a source of radiation (20); a plurality of detectors (30), arranged for receiving radiation emitted by the source along a plurality of respective paths (26); the apparatus configured such that, a structure (100) to be scanned is positionable between the detectors and the source; collimation elements (40) including a plurality of collimator channels (42), each located between a respective detector and the source; and collimation adjustment element (60). The apparatus, in a first configuration, provides a first resolution (r1) in an axial direction substantially orthogonal to a plane including the source and plurality of paths; and, in a second configuration, the collimation adjustment element is positioned between the collimation elements and the (Continued)

source such that the apparatus provides a second resolution (r2) in the axial direction; wherein r2<r1.

11 Claims, 4 Drawing Sheets

(52) U.S. Cl.
CPC . *G01N 2223/419* (2013.01); *G01N 2223/628* (2013.01); *G01N 2223/646* (2013.01)

(56) References Cited

U.S. PATENT DOCUMENTS

| | | | | |
|---|---|---|---|---|
| 2013/0163715 | A1* | 6/2013 | Kurochi | A61B 6/00 |
| | | | | 378/19 |
| 2014/0119508 | A1* | 5/2014 | Kang | G21K 1/025 |
| | | | | 378/62 |

FOREIGN PATENT DOCUMENTS

| | | |
|---|---|---|
| EP | 0 273 670 A2 | 7/1988 |
| EP | 0 461 776 A2 | 12/1991 |
| EP | 2 076 760 B1 | 7/2009 |
| GB | 2496736 A | 5/2013 |
| WO | 2013/064838 A1 | 5/2013 |

OTHER PUBLICATIONS

GB Search Report, dated Jun. 3, 2014, from corresponding GB application.

\* cited by examiner

APPARATUS AND METHOD FOR SCANNING A STRUCTURE

The present invention relates to an apparatus and method for scanning a structure and relates in particular, but not exclusively to an apparatus and method for scanning a structure to detect variations in density of the structure. The apparatus and method of the invention have particular benefits for use in an undersea pipeline inspection apparatus.

It is known to use gamma radiation for scanning structures, for example to obtain information about the density within the structure or to identify flaws such as cracks or corrosion in a structure. This is particularly useful for inspecting pipes subsea, where it is not always possible to inspect the pipe from the interior. Gamma scanning is also used for obtaining information about other industrial structures such as distillation columns and the like.

An apparatus for scanning structures such as a pipeline or process vessel using gamma radiation is described in GB 2496736 A. This apparatus comprises a source of gamma radiation and an array of detectors. The apparatus is capable of being arranged with the structure to be scanned, such as a pipeline, positioned between the source and detectors so that radiation emitted by the source can pass along a plurality of paths through a portion of the structure to the detectors. The number of detectors in the array may range from fewer than 10 up to more than 100, e.g. up to 150, depending on the application.

A typical detector for detecting gamma radiation comprises a scintillating crystal. Gamma rays entering the crystal interact with the scintillating material to produce photons in the visible and/or ultraviolet region. These scintillation photons are detected using a photodetector, for example a photomultiplier tube, which outputs an electrical pulse providing information about the number and energy of the incident gamma photons. Counting the number of gamma photons transmitted from the source to the detectors, through the structure being scanned, enables differences in the density of different parts of the structure to be detected.

To obtain high resolution data, a large number of detectors are used, closely spaced from one another. The detectors are arranged in an arc centred on the structure to be scanned. In operation, the source and array of detectors are arranged in fixed relationship with respect to each other, and are rotated around the structure to be scanned. In this way, information about the density of the structure along a plurality of paths is obtained, enabling a high resolution density map of the structure to be calculated. The apparatus may also be translated axially to scan different sections of the structure. This technique has similarities with medical imaging techniques such as x-ray tomography.

In order to detect the gamma radiation that has passed through the structure it is necessary to use detectors of sufficient size and density to stop the gamma photons so that they do not pass through the detector undetected. To maintain a high resolution, the radiation travelling towards each detector is typically collimated to reduce detection of gamma photons which have been scattered from a path other than the direct path from the source to a particular detector. The detection of scattered photons is generally further reduced by providing shielding material around the detectors so that the non-detecting surfaces of the detector, except for the portion of the collecting surface in optical communication with the photodetector, are protected from radiation. These requirements present constraints on the number and arrangement of the detectors and collimators.

In subsea applications, additional constraints arise. When operating at a depth of 1000 meters underwater, the pressure is 100 atmospheres and increases by a further 100 atmospheres for each additional 1000 meters of depth. The apparatus must be able to withstand this pressure yet remain sufficiently compact for deployment using remotely operated vehicles capable of operating at the required depth.

Preferred embodiments of the present invention seek to overcome one or more disadvantages of the prior art.

According to a first aspect of the invention there is provided an apparatus for scanning a structure for detecting variations in density of a structure, the apparatus comprising:
 a source of radiation;
 a plurality of detectors, arranged for receiving radiation emitted by said source along a plurality of respective paths;
 wherein said apparatus is configured such that, in use, a structure to be scanned is positionable between said detectors and said source;
 collimation means comprising a plurality of collimator channels, each located between a respective detector and said source; and
 collimation adjustment means;
 wherein, in a first configuration of said apparatus, said apparatus provides a first resolution in an axial direction substantially orthogonal to a plane passing through said source and said plurality of paths;
 wherein, in a second configuration of said apparatus, said collimation adjustment means is positioned between said collimation means and said source such that said apparatus provides a second resolution in said axial direction,
 wherein said second resolution is smaller than said first resolution.

Scanning a structure at a smaller resolution (i.e. to detect smaller artefacts) increases the scanning time required. For example, reducing the resolution by a factor of five reduces the amount of radiation reaching a detector by a factor of five, thereby reducing count rate and increasing the scanning time required at each axial position by a factor of five. At the same time, the axial length of structure scanned at each axial position is reduced by a factor of five, such that five times as many images are required to scan the complete structure. Therefore, the total measurement time increases by a factor of twenty-five. For many applications, this increase in overall scan time is unacceptable.

By providing collimation adjustment means, positionable between said collimation means and said source to provide a second resolution in said axial direction, smaller than a first resolution in said axial direction, the present invention enables a structure to be selectively scanned at two different resolutions when required. Advantageously, this enables the structure to be scanned at a relatively high rate at the first axial resolution when this is sufficient, while also enabling parts of the structure to be scanned at the second, smaller axial resolution when required, for example when small artefacts in the structure are detected.

In one embodiment, the axial direction is substantially orthogonal to a plane substantially centred on or aligned with the plurality of paths.

In one embodiment, the collimation adjustment means is selectively positionable between said collimation means and said source.

This means the collimation adjustment means may be removable from the apparatus when not required. This may reduce the complexity of the apparatus, as it may avoid introducing further moving parts are required.

The first resolution may be determined by said detectors and/or said collimation means.

In another embodiment, the collimation adjustment means is selectively positionable in a first position, corresponding to said first configuration, and in a second position, corresponding to said second configuration.

In said first configuration, the first resolution may be determined, at least in part, by the collimation adjustment means.

In some embodiments, said collimation adjustment means may comprise at least one plate or block.

At least one said plate or block may be moveable between a first position, corresponding to said first configuration of the apparatus, and a second position, corresponding to said second configuration of the apparatus.

The apparatus may further comprise at least one actuator for moving said plate or block between said first and second positions.

The collimation adjustment means may comprise at least one pair of plates or blocks, arranged to define a slit between their edges.

At least one said pair of plates or blocks may comprise a plate or block which is fixed relative to said collimation means.

At least one said plate or block may be curved.

At least one said plate or block may be coupled to said collimation means.

Said collimation adjustment means may extend across more than one said collimator channel.

Advantageously, by extending across more than one collimator channel, the collimation adjustment means may be used to adjust the resolution in said axial direction for more than one, or all, detectors simultaneously.

In said second configuration, said collimation adjustment means may be positioned, in use, between said collimation means and said structure to be scanned.

Advantageously, this enables the apparatus to remain compact, which is an important criterion for applications such as scanning subsea structures.

The apparatus may further comprise processing means for processing signals to detect artefacts in said structure, and actuation means for moving said collimation adjustment means between a first position and a second position in response to detecting an artefact in said structure.

Advantageously, this automates deployment of the collimation adjustment means.

The collimator channels may be substantially aligned with respective radii of a circle centred on said source.

In use, the detectors and the source may be rotatable in a fixed relationship with respect to each other about said structure.

The source may be a gamma radiation source.

According to a second aspect of the invention, there is provided a method for scanning a structure for detecting variations in density of a structure, the method comprising:
providing a source of radiation;
providing a plurality of detectors, arranged for receiving radiation emitted by said source along a plurality of respective paths;
arranging the apparatus such that a structure to be scanned is positioned between said detectors and said source;
providing collimation means comprising a plurality of collimator channels, each located between a respective detector and said source; and
providing collimation adjustment means;
wherein, in a first configuration of said apparatus, said apparatus provides a first resolution in an axial direction substantially orthogonal to a plane passing through said source and said plurality of paths;
wherein, in a second configuration of said apparatus, said collimation adjustment means is positioned between said collimation means and said source such that said apparatus provides a second resolution in said axial direction,
wherein said second resolution is different from said first resolution;
said method further comprising:
scanning a part of said structure with said apparatus in said first configuration; and
scanning a part of said structure with said apparatus in said second configuration.

Preferred embodiments of the present invention will now be described, by way of example, and not in any limitative sense, with reference to the accompanying drawings, in which.

With reference to FIGS. 1-5, a first embodiment of an apparatus according to the present invention will now be described.

Figure 1:
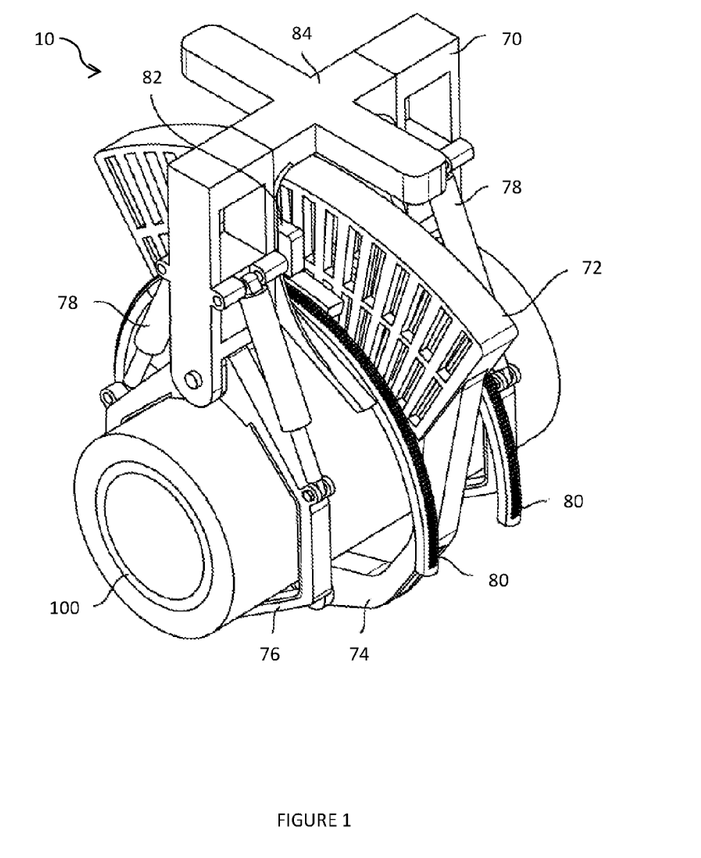
FIG. 1 shows a perspective view of an apparatus according to an embodiment of the invention.

The apparatus 10 is for scanning a structure 100, such as a subsea pipeline 100, for detecting variations in density of the structure 100. The apparatus 10 comprises a source of radiation 20 (FIGS. 2 and 4) and a plurality of detectors 30 arranged for receiving radiation emitted by the source 20. The apparatus 10 is configured such that, in use, the structure 100 to be scanned is positioned between the detectors 30 and the source 20 so that at least some paths of radiation emitted by the source 20 and received by the detectors 30 pass through the structure 100.

In this embodiment, the radiation source 20 is a gamma radiation source, such as $^{137}$Cs which has a characteristic emission at 661.7 keV, with sufficient penetrating power for scanning dense structures such as subsea pipelines. Other radiation sources may be used, including gamma radiation sources such as $^{60}$Co or $^{192}$Ir. The source 20 is surrounded by a source collimator 22 having a slot for collimating radiation from the source 20 in a fan shaped beam 24 towards the detectors 30. The source collimator 22 is preferably formed of a material which is highly attenuating to the radiation emitted by the source, for example a heavy alloy material. Although the present embodiment is based on gamma photon detection, it will be appreciated that the present invention can be applied to other types of radiation (e.g. neutrons).

The detectors 30 each comprise a scintillating material or crystal 32 suitable for detecting gamma photons at this source energy, for example BGO (bismuth germanate). Photodetectors 34 are provided for receiving light emitted by each respective scintillation crystal 32 and outputting an electrical signal in response to the light received from the scintillating material 32. Processing and analysis of the electrical signals output by the photodetectors 34 is performed to obtain an image of the structure 100 being scanned. The skilled person will appreciate that other combinations of sources and detectors may be used as is known in the art.

The apparatus 10 comprises collimation means 40 in the form of two collimator blocks 40, each comprising a plurality of collimator channels 42. Each collimator channel 42 is located between a respective detector 30 and the source 20 for collimating radiation travelling towards each detector 30 in order to reduce the detection of gamma photons which have been scattered from a path other than a direct path from the source 20 to the respective detector 30. The collimator channels 42 are substantially centred on a plane passing through the source 20, that is, the plane of FIG. 2. More particularly, the collimator channels 42 are substantially aligned with respective radii of a circle centred on the source 20.

For an apparatus for scanning a cylindrical structure such as a pipeline 100, it is preferred that the detectors 30 are arranged approximately in an arc having an origin which is not the source 20, but which is centred on the pipe 100 and/or axis of rotation 50. This is convenient for rotation of the detectors 30, collimators 40 and the source 20 around the pipe structure 100. However, since the collimator channels 42 are all directed towards the source 20 and not towards the axis of rotation 50, this means that most of the collimator channels 42 are not perpendicular to a tangent to that arc.

Figure 2:
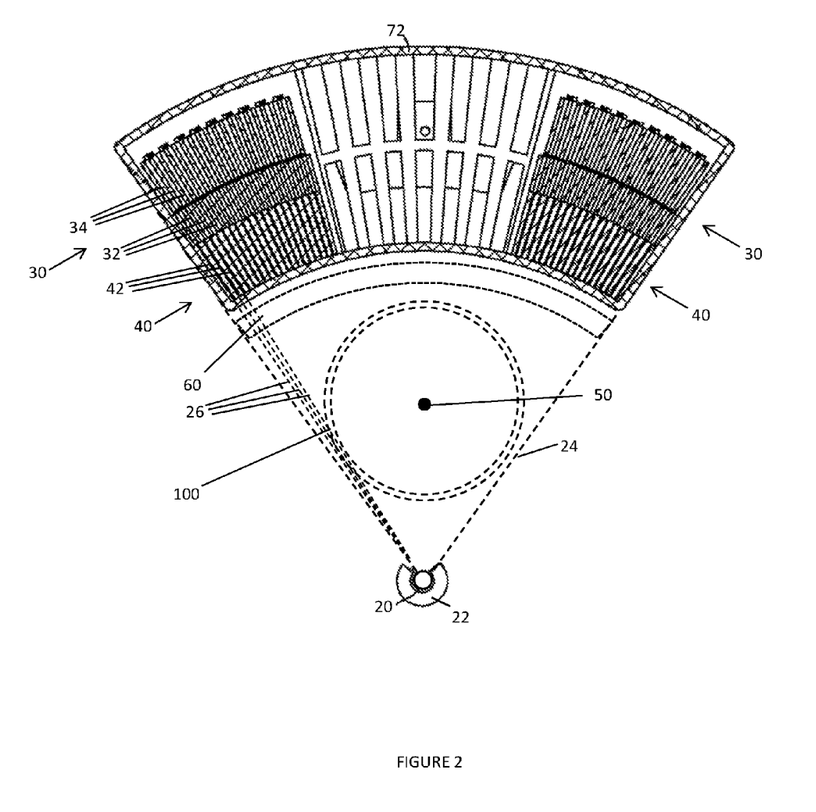
FIG. 2 is a diagrammatic cross-sectional representation of an apparatus according to an embodiment of the invention.

By using multiple detectors 30, multiple different paths 26 through the structure 100 may be scanned simultaneously. Each detector 30 and associated collimator channel 42 defines a different path 26 through the structure 100. For clarity only three radiation paths 26 are shown in FIG. 2, between the source 20 and detectors 30, via three respective collimator channels 42 of the left-hand collimator block 40. The number of radiation paths which may be scanned simultaneously is determined by the number of detectors 30. Each path 26 is defined by a volume bounded by the surface of the source 20 at one end, the detection area of the detector 30 at the other, and having a cross-section limited by the detection area of the detector 30, the cross-sectional area of the collimator channel 42 and/or the exposed area of the source 20. In this embodiment, the detectors 30 have a rectangular detection area. By approximating the surface of the spherical source 20 to a plane, the shape of the paths 26 can be approximated to a rectangular frustrum.

The collimator block 40 is formed of a shielding material which is attenuating to gamma radiation. A dense shielding material such as lead, tungsten, or a heavy alloy may be used, which is highly attenuating to gamma radiation. Alternatively, a less dense material such as steel may be used. This provides less shielding but is not as heavy as the denser shielding materials. The length of each collimator channel 42 is determined by the requirements of the detectors 30, the energy of radiation emitted by the source 20, and the shielding material used. The collimator channels 42 may be any convenient shape, although it is preferred that the cross-sections of the channels 42 have the same shape and orientation as the detecting surfaces of the respective detectors 30.

The collimator blocks 40 also include recesses for receiving the detectors 30, which fixes the relative positions of the detectors 30 and collimator channels 42. However, in other embodiments, the detectors 30 may be housed separately from the collimator channels 42. The detecting surfaces of the detectors 30 are accessible to radiation passing through the respective collimator channel 42. A portion of the detecting surface of each detector 30 (e.g. a portion of the surface of the scintillating material 32) may be covered by shielding material of the collimator block 40, for the purposes of delimiting the area of the detecting surface or for mechanically retaining the detector 30 within the collimator block 40. The non-detecting surfaces of the detectors 30 are shielded from incident radiation by the shielding material of the collimator blocks 40.

In the present embodiment, the collimator channels 42 and detectors 30 are provided in two separate collimator blocks 40. The arrangement shown is suited to scanning the walls of a pipeline 100. However, a single collimator block may be provided, and may be centrally located opposite the source 20. This is more suitable for scanning the contents of a pipeline 100.

In use, the detectors 30, collimators 40 and source 20 are rotated in a fixed relationship relative to each other about an axis of rotation 50 located between the source 20 and detectors 30. The axis of rotation 50 is substantially centred on the structure 100 to be scanned.

A perspective view of the apparatus 10 is shown in FIG. 1, positioned for scanning a pipe 100. The apparatus includes a support 70 which supports a detector housing 72 and source unit 74. The detector housing 72 houses the detectors 30, collimators 40 and associated electronics, and is sealed for use underwater. The source unit 74 houses the source 20 and source collimator 22. Clamping members 76, actuated by arms 78, enable the apparatus 10 to be clamped around the pipe 100. The apparatus 10 also includes rails 80 supporting the detector housing 72 and source unit 74. A motor 82, mounted on the detector housing 72, is operable to move the detector housing 72 and source unit 74 along the rails 80 and thereby to rotate the position of the source 20 and detectors 30 around the pipeline 100. At each position, radiation emitted by the source 20 towards each detector 30 forms a number of radiation paths through the walls of the pipe 100. Rotation of the source 20 and detectors 30 around the pipe 100 enables further paths to be scanned. Data in the form of counts detected by the detectors 30 is processed and stored by a data processor in housing 84 located towards the top of the support 70. The apparatus may be translated in an axial direction, i.e. along the pipe 100, to scan different parts of the pipe 100.

FIG. 2 represents a cross-sectional view of the apparatus, across a plane through the centre of the detector housing 72 and source 20. Collimation adjustment means 60, in the form of a slit collimator 60, can be positioned in front of the collimator blocks 40 in the position indicated. When the slit collimator 60 is not present, the resolution obtained in an axial direction (that is, orthogonal to the plane of FIG. 2) is determined by the configuration of the detectors 30 and/or collimator channels 42. The axial direction is orthogonal to a plane passing through the source 20, collimator channels 42 and detectors 30, i.e. orthogonal to the plane of FIG. 2. Equivalently, the axial direction is parallel to the axis of rotation 50. When positioned for use, the collimation adjustment means 60 provides a second resolution in the axial direction which is smaller than the first resolution obtained when the slit collimator 60 is not in use. By smaller resolution, we mean that the apparatus is able to resolve smaller features.

Figure 3:
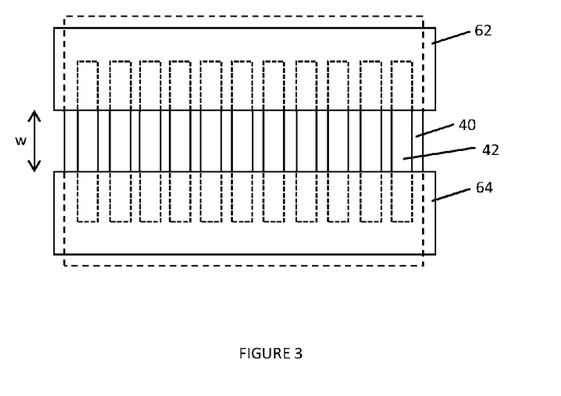
FIG. 3 is a diagrammatic representation of a front view of a collimator unit suitable for an apparatus according to an embodiment of the invention.

With reference to FIG. 3, the collimation adjustment means 60 according to one embodiment is a slit collimator comprising a first plate 62 and a second plate 64, positionable in front of the collimator 40. For clarity, the collimator 40 is shown in FIG. 3 as a single block 40 comprising eleven collimator channels 42. However, in practice, the number of detectors 30 and collimator channels 42 may vary from fewer than 10 to more than 80, e.g. up to 150 or more, depending on the application for which the scanning method is to be used.

With reference to FIGS. 2 and 3, the plates 62, 64 extend across the entire collimator 40, that is, across all the collimator channels 42. However, in alternative embodiments, multiple pairs of plates 62, 64 may be provided. For example, a separate pair of plates 62, 64 may be provided for each collimator block 40 when multiple collimator blocks are used. The plates 62, 64 may be curved to follow the shape of the arrangement of detectors 30 and collimator 40, as shown in FIG. 2. However, this may not be necessary, especially if multiple pairs of plates 62, 64 are provided.

Figure 4:
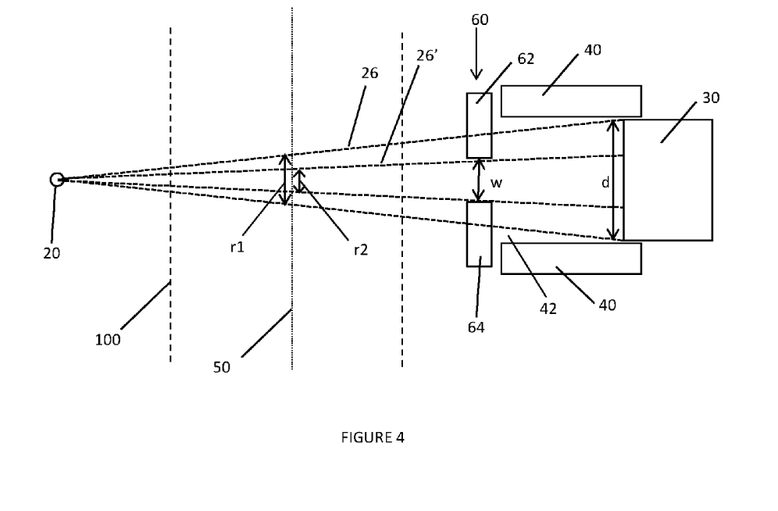
FIG. 4 is a diagrammatic cross-sectional representation of an apparatus according to an embodiment of the invention.

FIG. 4 is a cross-sectional view of a plane through the source 20 and one of the collimator channels 42. FIG. 4 shows the effect of the slit collimator 60 on the axial resolution of an image of the scanned structure 100. The slit collimator 60 limits the axial extent of the beam of radiation 26 arriving at the detectors. The structure 100 being scanned is located approximately half way between the source 20 and detectors 30.

When the slit collimator 60 is not present, the extent of the beam of radiation 26 reaching the detector 30 in an axial direction is limited by the first collimator channel 42 and/or the axial extent d of the detection area of the detector 30. The collimator channels 42 may have substantially rectangular openings, as shown in FIG. 3. Given that the axial width of the beam of radiation arriving at each detector 30 varies along the radiation path, the axial resolution obtained also varies along the path. However, given that the structure 100 being scanned is located approximately half way between the source 20 and detectors 30, and since the source 20 can be approximated as a point source, the first resolution obtained in an axial direction is approximately half the size of the detection area/collimator width d in the axial direction. This first resolution is indicated in FIG. 4 as the axial size r1, at the position of the axis of rotation 50 (that is, approximately at the centre of the structure 100 being scanned), of the beam 26 of radiation received at the detector 30. In one embodiment, the detectors have an axial length d of about 30 mm, leading to a first resolution r1 in the axial direction of about 15 mm.

When the slit collimator 60 is positioned for use, as shown in FIG. 4, the beam of radiation 26' received at the detector 30 is limited to a smaller angle in the axial direction because the slit width w of the collimator 60 is narrower than the axial width d of the detection area. This reduces the image resolution accordingly. This second resolution is indicated in FIG. 4 as the axial size r2, at the position of the axis of rotation 50 (that is, approximately at the centre of the structure 100 being scanned), of the beam 26' of radiation received at the detector 30 when the slit collimator 60 is positioned for use. In one embodiment, the slit collimator has a slit width w of about 6 mm, leading to a second resolution r2 in the axial direction of about 3 mm.

Regardless of the position of the slit collimator 60, the collimator channels 42 continue to shield the detectors 30 from scattered photons.

Since the slit collimator 60 reduces the size of the aperture for radiation arriving at the detector 30 the count rate drops significantly. It is therefore important that the plates 62, 64 are very efficient in blocking photons. The thickness of the plates 62, 64 must therefore be selected carefully depending on the slit width of the slit collimator 60 and the material used. For a 6 mm slit opening, it has been found that 15 mm thick tungsten plates provide sufficient contrast between the 'blank' region of the plates 62, 64 and the 'slit' region between the plates 62, 64.

In one embodiment, the plates 62, 64 may be fixed in place when required, for example by bolting them onto the detector housing 72 or collimator blocks 40 when required.

Figure 5:
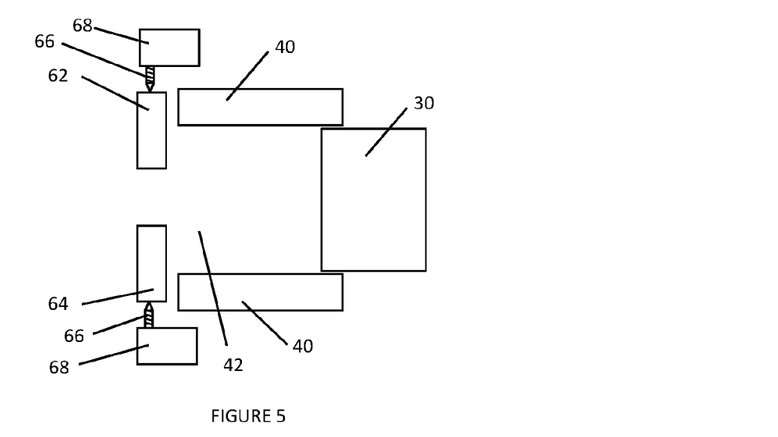
FIG. 5 is a diagrammatic cross-sectional representation of an apparatus according to an embodiment of the invention.

FIG. 5 shows another embodiment of the invention, in which the plates 62, 64 are moveable by means of an actuator 68 comprising, for example, a motor and guide screws 66. The actuator may be electrically or hydraulically driven. The actuator may be controlled remotely to move the plates 62, 64 between respective first positions, to provide a first axial resolution, and respective second positions, to provide a second axial resolution. In their respective second positions, the plates 62, 64 define a smaller slit width w than in their first positions. The actuator may be controlled automatically by a controller in response to detecting an artefact, identified by a detector signal having particular characteristics. For example, the actuators 68 may be driven to move the plates 62, 64 from the respective first positions to the respective second positions to record finer detail when measurements fall outside predetermined limits, for example when wall thinning of the structure 100 is detected.

In their respective first positions, the plates 62, 64 may be retracted so that they do not obstruct the collimator channels 42, such that the first axial resolution is determined by the axial width d of the collimator channels and/or detection area of the detectors 30. Alternatively, the plates 62, 64 may partially obstruct the collimator channels 42 in their respective first positions, such that the first axial resolution is determined by a first separation w of the plates 62, 64. In the second position, the second axial resolution is determined by a second separation w between the plates 62, 64, which is smaller than the first separation and the axial width d of the collimator channels and/or detection area of the detectors 30.

Figure 6:
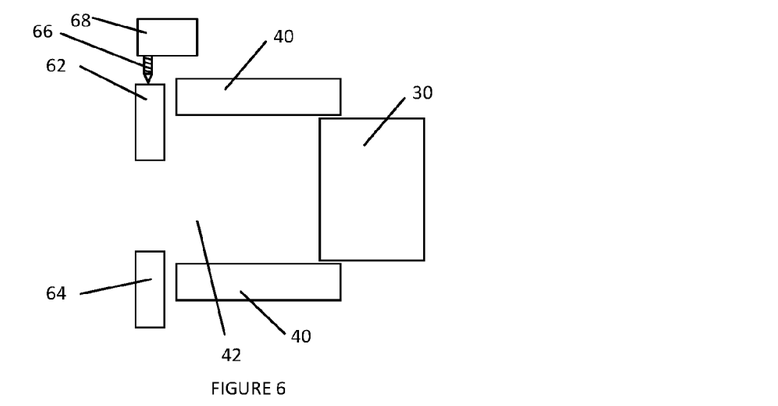
FIG. 6 is a diagrammatic cross-sectional representation of an apparatus according to another embodiment of the invention.

FIG. 6 shows another embodiment of the invention. In this embodiment, one plate 62 is moveable by means of an actuator 68 as described above, while the other plate 64 is fixed. The second plate 64 may slightly obstruct the collimator channels 42.

Figure 7:
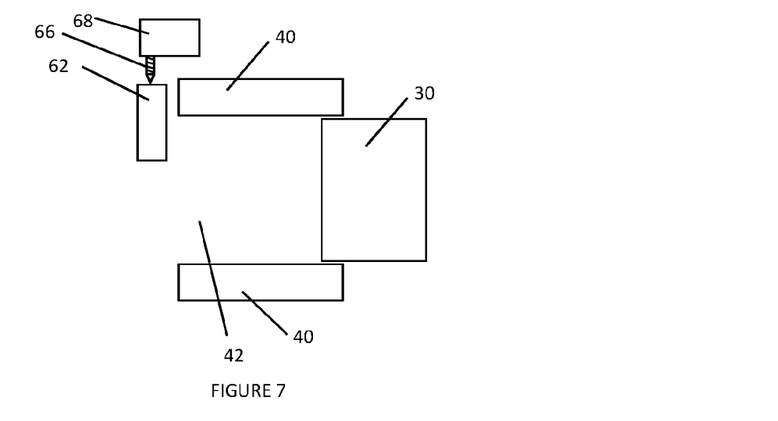
FIG. 7 is a diagrammatic cross-sectional representation of an apparatus according to a further embodiment of the invention.

FIG. 7 shows a further embodiment of the invention. In this embodiment, the slit collimator 60 comprises a single plate 62. The plate 62 is moveable by means of an actuator 68 as described above between a first position and a second position. In the second position, the second axial resolution is determined by a separation between the plate 62 and the opposing side of the collimator channels 42.

It will be appreciated by persons skilled in the art that the above embodiments have been described by way of example only, and not in any limitative sense, and that various alterations and modifications are possible without departure from the scope of the invention as defined by the appended claims.

The invention claimed is:

1. An apparatus for scanning a subsea pipeline for detecting variations in density of the subsea pipeline, the apparatus comprising:
   a source of gamma radiation;
   a plurality of detectors, arranged for receiving gamma radiation emitted by said source along a plurality of respective paths;
   wherein said apparatus is configured such that, in use, a structure to be scanned is positionable between said detectors and said source;

collimation means comprising a plurality of collimator channels, each located between a respective detector and said source; and collimation adjustment means wherein said collimation adjustment means comprises at least one pair of plates or blocks, arranged to define a slit between their edges and extending across more than one said collimator channel;

wherein, at least one said plate or block is moveable between a first position corresponding to a first configuration of said apparatus, in which said apparatus provides a first resolution in an axial direction substantially orthogonal to a plane passing through said source and said plurality of paths, and a second position corresponding to a second configuration of said apparatus, in which said collimation adjustment means is positioned between said collimation means and said subsea pipeline to be scanned such that said apparatus provides a second resolution in said axial direction;

wherein said second resolution is smaller than said first resolution.

2. The apparatus according to claim 1, wherein said first resolution is determined by said detectors and/or said collimation means.

3. The apparatus according to claim 1, wherein, in said first configuration, said first resolution is determined, at least in part, by said collimation adjustment means.

4. The apparatus according to claim 1, further comprising at least one actuator for moving said plate or block between said first and second positions.

5. The apparatus according to claim 1, wherein at least one said pair of plates or blocks comprises a plate or block which is fixed relative to said collimation means.

6. The apparatus according to claim 1, wherein at least one said plate or block is curved.

7. The apparatus according to claim 1, wherein at least one said plate or block is coupled to said collimation means.

8. The apparatus according to claim 1, further comprising processing means for processing signals to detect artefacts in said structure, and actuation means for moving said collimation adjustment means between a first position and a second position in response to detecting an artefact in said structure.

9. The apparatus according to claim 1, wherein said collimator channels are substantially aligned with respective radii of a circle centred on said source.

10. The apparatus according to claim 1, wherein, in use, said detectors and said source are rotatable in a fixed relationship with respect to each other about said structure.

11. A method for scanning a subsea pipeline for detecting variations in density of the subsea pipeline, the method comprising:

providing a source of gamma radiation;

providing a plurality of detectors, arranged for receiving gamma radiation emitted by said source along a plurality of respective paths;

arranging the apparatus such that a structure to be scanned is positioned between said detectors and said source;

providing collimation means comprising a plurality of collimator channels, each located between a respective detector and said source; and providing collimation adjustment means wherein said collimation adjustment means comprises at least one pair of plates or blocks, arranged to define a slit between their edges and extending across more than one said collimator channel;

wherein, in at least one said plate or block is moveable between a first position corresponding to a first configuration of said apparatus, in which said apparatus provides a first resolution in an axial direction substantially orthogonal to a plane passing through said source and said plurality of paths, and a second position corresponding to a second configuration of said apparatus, in which said collimation adjustment means is positioned between said collimation means and said subsea pipeline such that said apparatus provides a second resolution in said axial direction, wherein said second resolution is smaller than said first resolution;

said method further comprising:

scanning a part of said subsea pipeline with said apparatus in said first configuration;

moving said at least one plate or block between said first position and said second position; and scanning a part of said subsea pipeline with said apparatus in said second configuration.

* * * * *